United States Patent [19]

Leyendecker et al.

[11] Patent Number: 5,541,185
[45] Date of Patent: Jul. 30, 1996

[54] 3(2H)-PYRIDAZINONE DERIVATIVES AND THEIR USE FOR CONTROLLING PESTS

[75] Inventors: Joachim Leyendecker, Ladenburg; Hans Theobald, Limburgerhof; Thomas Kuekenhoehner, Frankenthal; Peter Hofmeister, Neustadt; Christoph Kuenast, Otterstadt; Norbert Goetz, Worms, all of Germany

[73] Assignee: BASF Aktiengesellschaft, Ludwigshafen, Germany

[21] Appl. No.: 369,289

[22] Filed: Jan. 6, 1995

Related U.S. Application Data

[63] Continuation of Ser. No. 652,201, Feb. 5, 1991, abandoned, which is a continuation of Ser. No. 448,841, Dec. 12, 1989, abandoned.

[30] Foreign Application Priority Data

Dec. 29, 1988 [DE] Germany ................ 38 44 227.2

[51] Int. Cl.[6] ........................................ A01N 43/58
[52] U.S. Cl. ........................................ 514/252; 544/238
[58] Field of Search ........................ 514/252; 544/238

[56] References Cited

U.S. PATENT DOCUMENTS

| | | | |
|---|---|---|---|
| 4,571,397 | 2/1986 | Taniguchi et al. | 514/252 |
| 4,820,704 | 4/1989 | Richarz et al. | 514/252 |
| 4,837,217 | 6/1989 | Ogura et al. | 514/252 |
| 4,874,861 | 10/1989 | Ogura et al. | 544/239 |
| 4,877,787 | 10/1989 | Taniguchi et al. | 514/247 |
| 4,929,617 | 5/1990 | Leyendecker et al. | 514/252 |
| 4,945,091 | 7/1990 | Makabe et al. | 544/238 |

FOREIGN PATENT DOCUMENTS

| | | |
|---|---|---|
| 607934 | 9/1961 | Belgium . |
| 0088384 | 9/1983 | European Pat. Off. . |
| 0134439 | 6/1984 | European Pat. Off. . |
| 0183212 | 6/1986 | European Pat. Off. . |
| 0190595 | 8/1986 | European Pat. Off. . |
| 0199281 | 10/1986 | European Pat. Off. . |
| 0320733 | 6/1989 | European Pat. Off. ........ 544/238 |
| 2249962 | 4/1974 | Germany . |
| 2754832.9 | 6/1979 | Germany . |
| 0199966 | 8/1989 | Japan ........................ 544/238 |
| 2087723 | 6/1982 | United Kingdom . |
| 86/00899 | 2/1986 | WIPO . |
| 86/00900 | 2/1986 | WIPO . |

OTHER PUBLICATIONS

Bertini, Vincenzo, J. C. S. Perkins I, pp. 570–571 (1976).
J. Org. Chem. vol. 26 (1961), p. 1541–1518.
Kaji et al, Chem. Pharm. Bull., vol. 18 (1970), p. 147+.
Sasaki et al, Bull. Chem. Soc. Jpn., vol. 40 (1967), p. 2604–2607 J. Chem. Soc., (1939), p. 1245–1247.
Traynuam et al. J. Am. Chem. Soc., vol. 90 (1968), pp. 5208–5210.
Della, Aust. J. Chem., vol. 23 (1970), pp. 2421–2426.
Snider et al J. Am. Chem. Soc., vol. 104 (1982), pp. 555–563.
Bartok et al Helv. Chim. Acta, vol. 63 (1980), pp. 2173–2177.
Ohloff et al Helv. Chim. Acta, vol. 66 (1983), pp. 1343–1354.
Ingold et al Perkin Trans. II (1986), pp. 1337–1344.
Angew. Chem./71. Jahrg. 1960/Nr, 22, pp. 864–865.

*Primary Examiner*—Donald G. Daus
*Attorney, Agent, or Firm*—Keil & Weinkauf

[57] ABSTRACT

3(2H)-Pyridazinone derivatives of the general formula I $$R^1-N\underset{\underset{N}{|}}{\overset{O}{\overset{\|}{C}}}\cdots\overset{X}{\underset{W-CH-Z,}{|}}\underset{R^2}{|} \quad (I)$$

where $R^1$ is alkyl, $R^2$ is hydrogen or alkyl, X is halogen, W is oxygen or sulfur and Z is a hetaryl-substituted isoxazolyl radical or a substituted or unsubstituted cyclohexyl or cyclopentyl radical, plant-tolerated salts thereof, processes for their manufacture, and their use as pesticides.

6 Claims, No Drawings

3(2H)-PYRIDAZINONE DERIVATIVES AND THEIR USE FOR CONTROLLING PESTS

The present application is a continuation of application Ser. No. 07/652,201, filed on Feb. 5, 1991, which was a continuation of application Ser. No. 07/448,841, filed on Dec. 12, 1989, both now abandoned.

The present invention relates to novel 3(2H)-pyridazinone derivatives of the general formula I

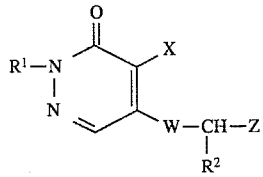 (I)

where $R^1$ is $C_1$–$C_8$-alkyl, $R^2$ is hydrogen or $C_1$–$C_4$-alkyl, X is halogen, W is oxygen or sulfur and Z is a hetaryl-substituted isoxazolyl radical

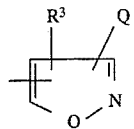

where $R^3$ is hydrogen, halogen, $C_1$–$C_8$-alkyl or $C_2$–$C_8$-alkenyl and Q is a 5-membered or 6-membered heterocyclic structure having 1 to 4 heteroatoms from the group consisting of nitrogen, oxygen and sulfur, which structure is unsubstituted or monosubstituted to trisubstituted by halogen, $C_1$–$C_8$-alkyl, $C_2$–$C_6$-alkenyl, $C_2$–$C_4$-alkynyl, $C_1$–$C_4$-haloalkyl, $C_1$–$C_8$-alkoxy, $C_2$–$C_8$-alkoxyalkyl, $C_3$–$C_8$-cycloalkyl, cyano or nitro, or Z is an unsubstituted or substituted $C_5$- or $C_6$-cycloalkyl radical

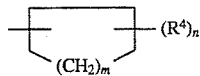

where $R^4$ is halogen, $C_1$–$C_{10}$-alkyl, $C_1$–$C_4$-haloalkyl, $C_1$–$C_4$-haloalkoxy, $C_1$–$C_8$-alkoxy, $C_2$–$C_8$-haloalkyl, $C_3$–$C_{10}$-cycloalkyl or $C_1$–$C_6$-dialkylamino, m is 1 or 2 and n is an integer of from 0 to 5, and $R^4$ is identical or different when n is greater than 1, and plant-tolerated salts of the 3(2H)-pyridazinone derivatives I.

The present invention furthermore relates to pesticides which contain the compounds I or their salts as active ingredients and a method for controlling pests.

The earlier German Patent Application P 37 42 266.9 describes 2-tert-butyl-5-isoxazolylmethylthio-3(2H)-pyridazinones which are phenyl- or aryl-substituted isoxazolyl radicals. EP-A-199 281 discloses many hetaryl-substituted 3(2H)-pyridazinones which, however, do not contain an isoxazolyl radical as the hetaryl radical. EP-A-88 384 (U.S. Pat. No. 4,571,397), EP-A-134 439 (U.S. Pat. No. 4,877, 757) and EP-A-183 212 (U.S. Pat. No. 4,874,861) furthermore disclose a large number of 5-benzyl-3(2H)-pyridazinone derivatives. However, the insecticidal and acaricidal action of the compounds described above is not always satisfactory.

It is an object of the present-invention to provide novel, specially substituted 3(2H)-pyridazinone derivatives having an improved action.

We have found that this object is achieved by the novel 3(2H)-pyridazinone derivatives defined at the out-set, of the general formula I, or their plant-tolerated salts, and a process for their preparation. We have furthermore found that the compounds I or their salts are very well tolerated by plants and are very useful for controlling pests.

The substituents in the formula I have the following specific meanings:

$R^1$ is straight-chain or branched $C_1$–$C_8$-alkyl, preferably $C_1$–$C_6$-alkyl, particularly preferably $C_1$–$C_4$-alkyl, such as methyl, ethyl, n-propyl, isopropyl, n-butyl, isobutyl, sec-butyl or tert-butyl, $R^2$ is hydrogen, straight-chain or branched $C_1$–$C_4$-alkyl as mentioned for $R^1$, preferably $C_1$- or $C_2$-alkyl, particularly preferably methyl, X is halogen, preferably chlorine or bromine, particularly preferably chlorine, W is oxygen or sulfur, particularly preferably sulfur, Z is an unsubstituted or substituted isoxazolyl radical in which $R^3$ is hydrogen, preferably hydrogen in the 4-position, halogen, preferably fluorine, chlorine or bromine, particularly preferably bromine in the 5-position, straight-chain or branched $C_1$–$C_8$-alkyl, preferably straight-chain or branched $C_1$–$C_4$-alkyl, particularly preferably methyl in the 5-position, or straight-chain or branched $C_2$–$C_6$-alkenyl, preferably straight-chain or branched $C_2$–$C_4$-alkenyl, particularly preferably vinyl, methylvinyl or dimethylvinyl, and Q is a 5-membered or 6-membered, monosubstituted to trisubstituted heterocyclic structure having 1 to 4, in particular 1 to 3, heteroatoms, such as nitrogen, oxygen or sulfur. Preferred heterocyclic structures are pyrrol-2-yl, pyrrol-3-yl, furan-2-yl, furan-3-yl, thiophen-3-yl, pyrazol-3-yl, pyrazol-4-yl, pyrazol-5-yl, imidazol-2-yl, imidazol-4-yl, imidazol-5-yl, 1,2,4-triazol-3-yl, 1,2,4-triazol-5-yl, isoxazol-3-yl, isoxazol-4-yl, isoxazol-5-yl, isothiazol-3-yl, isothiazol-4-yl, isothiazol-5-yl, oxazol-2-yl, thiazol-2-yl, thiazol-4-yl, thiazol-5-yl, 1,3,4-oxadiazol-2-yl, 1,3,4-thiadiazol-2-yl, 1,2,4-oxadiazol-3-yl, 1,2,4-oxadiazol-5-yl, pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, 1,2,3-triazin-4-yl, 1,2,3-triazin-5-yl, 1,2,4-triazin-3-yl, 1,2,4-triazin-5-yl, 1,2,4-triazin-6-yl, 1,3,5-triazin-2-yl, tetrahydro-furan-2-yl, tetrahydrofuran-3-yl, piperidin-2-yl, piperidin-3-yl, piperidin-4-yl, tetrahydropyran-2-yl, tetrahydropyran-3-yl, tetrahydropyran-4-yl, tetrahydro-thiopyran-2-yl, tetrahydrothiopyran-3-yl, tetrahydrothiopyran-4-yl, particularly preferably pyrrol-2-yl, pyrrol-3-yl, furan-2-yl, furan-3-yl, thiophen-2-yl, thiophen-3-yl, imidazol-4-yl, pyrazol-3-yl, pyrazol-4-yl, pyrazol-5-yl, isoxazol-3-yl, isoxazol-4-yl, isoxazol-5-yl, isothiazol-4-yl, thiazol-4-yl, thiazol-5-yl, 1,2,4-oxadiazol-3-yl, 1,2,4-oxadiazol-5-yl, 1,3,4-thiadiazol-2-yl, 1,3,4-oxadiazol-2-yl, pyridin-2-yl, pyridin-3-yl, pyridin-4-yl, pyrazin-2-yl, pyrimidin-4-yl, pyrimidin-5-yl, tetrahydropyran-2-yl, tetrahydropyran-3-yl, tetrahydropyran-4-yl and tetrahydrothiopyran-3-yl being preferred, and suitable substituents being halogen, preferably fluorine, chlorine or bromine, particularly preferably chlorine or bromine, $C_1$–$C_8$-alkyl, preferably $C_1$–$C_4$-alkyl, particularly preferably methyl, ethyl, isopropyl or tert-butyl, $C_2$–$C_8$-alkenyl, preferably $C_2$–$C_4$-alkenyl, particularly preferably ethenyl, 1-methylethenyl, propenyl, 2-methylpropenyl, $C_1$–$C_4$-haloalkyl, preferably fluorine- or chlorine-substituted $C_1$- or $C_2$-haloalkyl, particularly preferably trifluoromethyl or 2,2,2-trifluoroeth-1-yl, $C_1$–$C_8$- alkoxy, preferably $C_1$–$C_3$-alkoxy, particularly preferably methoxy, ethoxy, n-propoxy or isopropoxy, $C_2$–$C_8$-alkoxyalkyl, preferably $C_2$–$C_4$-alkoxyalkyl, particularly preferably methoxymethyl, 1-methoxyethyl, 2-methoxyethyl or 1-methoxypropyl, $C_3$–$C_8$-cycloalkyl, preferably $C_3$–$C_5$-cycloalkyl, such as cyclopropyl, cyclobutyl or cyclopentyl, cyano or nitro, Z is unsubstituted or substituted $C_5$- or $C_6$-cycloalkyl in which $R^4$ is halogen, preferably fluorine, chlorine or bromine, particularly preferably chlorine or bromine, straight-chain or branched $C_1$–$C_{10}$-alkyl, preferably $C_1$–$C_8$-alkyl, particularly preferably $C_1$–$C_4$-alkyl, such as methyl, ethyl, n-propyl, isopropyl, n-butyl, isobutyl, sec-butyl or tert-butyl, straight-chain or branched $C_1$–$C_4$-haloalkyl, preferably $C_1$- or $C_2$-haloalkyl, particularly preferably $C_1$- or $C_2$-fluoro- or chloroalkyl, such as fluoromethyl, difluoromethyl, trifluoromethyl, chloromethyl, dichloromethyl, trichloromethyl, chlorofluoromethyl, dichlorofluoromethyl, 2,2,2-trifluoroethyl or 2,2,2-trichloroethyl, straight-chain or branched $C_1$–$C_8$-alkoxy, preferably $C_1$–$C_6$-alkoxy, particularly preferably $C_1$–$C_4$-alkoxy, such as methoxy, ethoxy, n-propoxy, isopropoxy, n-butoxy, isobutoxy, sec-butoxy or tert-butoxy, straight-chain or branched $C_2$–$C_8$-alkoxyalkyl, preferably $C_2$–$C_6$-alkoxyalkyl, particularly preferably $C_2$–$C_4$-alkoxyalkyl, such as methoxymethyl, ethoxymethyl, n-propoxymethyl, isopropoxymethyl, 1-methoxyethyl, 2-methoxyethyl, 1-ethoxyethyl, 2-ethoxethyl, 1-n-propoxyethyl, 2-n-propoxyethyl, 1-isopropoxyethyl, 2-isopropoxyethyl, 1-methoxy-n-propyl, 2-methoxy-n-propyl, 3-methoxy-n-propyl, 1-methoxyisopropyl or 2-methoxyisopropyl, $C_3$–$C_{10}$-cycloalkyl, preferably $C_3$–$C_8$-cycloalkyl, particularly preferably $C_3$–$C_6$-cycloalkyl, such as cyclopropyl, cyclobutyl, cyclopentyl or cyclohexyl, branched or straight-chain $C_1$–$C_6$-dialkylamino, preferably $C_1$–$C_4$-dialkylamino, particularly preferably $C_1$- or $C_2$-dialkylamino, such as dimethyl- or diethylamino, and n is from 0 to 5, preferably from 1 to 4, particularly preferably from 1 to 3, and $R^4$ may be identical or different when n is 2 or 3.

The compounds I are obtainable by the following method: A 3(2H)-pyridazinone derivative of the general formula II is reacted with an isoxazole of the general formula IIIa or with a cycloalkane derivative IIIb in the presence of a base at from −20° to 250° C., preferably from 20° to 120° C. in accordance with the following equations:

a)

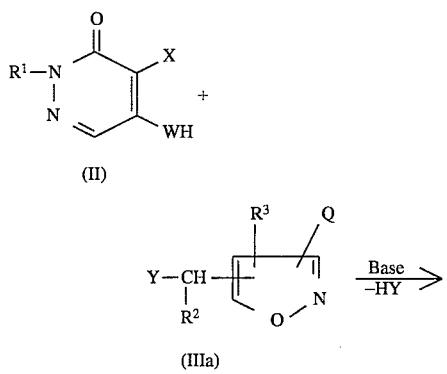

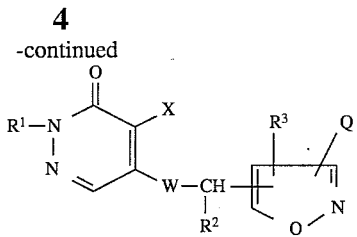

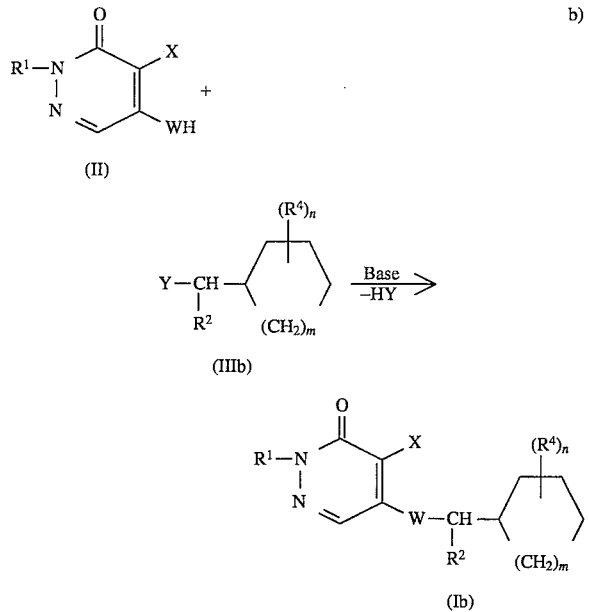

The 3(2H)-pyridazinone derivatives of the general formula II are described in Belgian Patent 607,934, in EP-A-134 439 (U.S. Pat. No. 4,877,787), in Angew. Chem. 72 (1960), 864 et seq. and in Chem. Pharm. Bull. 18 (1970), 147 et seq. or can be prepared by the methods described there.

The isoxazoles of the formula IIIa are disclosed in Bull. Chem. Soc. Jpn. 40 (1967), 2604–2607; WO-A-86/899; WO-A-86/900; J. Her. Chem. 19 (1982), 557–560; J. Chem. Soc. Perkin Trans I. 1976, 570–573, and J. Org. Chem. 26 (1961), 1514–1518, or can be prepared by the methods described in DE-A-25 49 962 and DE-A-27 54 832 (U.S. Pat. No. 3,213,068) from aldoximes by 1,3-dipolar cycloaddition with propargyl alcohols or propargyl halides.

In *Bull. Chem. Soc. Jpn.*, 40 (1967), pp. 2604–2607, the manufacture of the following compounds (IIIa) is described: Table 2, Case No. XI, 2a:

Table 2, Case No. XI, 2a:

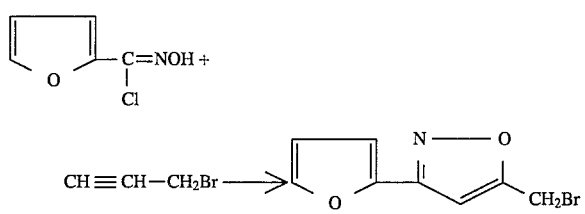

Table 2, Case No XII, 2b:

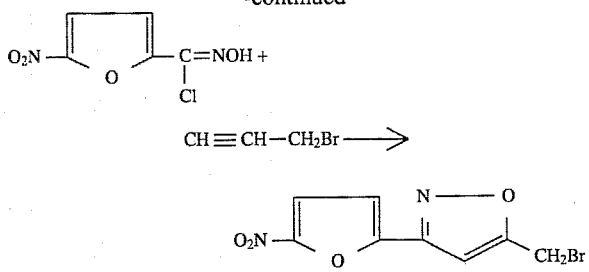

Table 2, Case No XII,
This means the manufacture of the following compounds (IIIa) are described:

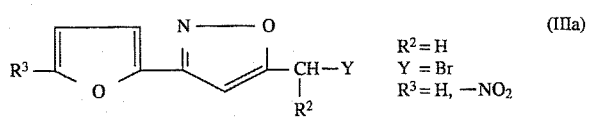

$$R^2 = H$$
$$Y = Br$$
$$R^3 = H, -NO_2$$

In addition in Table 2, case XIII, 2b the manufacture of the following compounds are described:

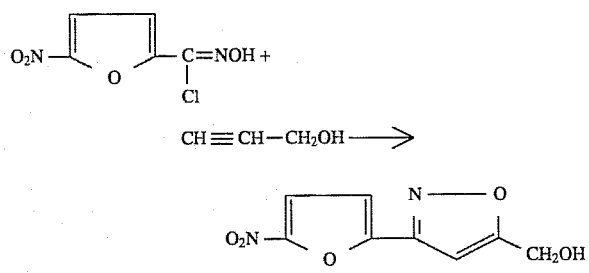

This means the manufacture of (IIIa) is shown except that Y is a hydroxy group.

The cycloalkane derivatives of the general formula IIIb are disclosed in J. Chem. Soc. 1939, 1245–1247; J. Am. Chem. Soc. 90 (1968), 5208–5210; Aust. J. Chem. 23 (1970), 2421–2426; J. Am. Chem. Soc. 104 (1982), 555–563; Helv. Chim. Acta 63 (1980), 2173–2178; Helv. Chim. Acta 66 (1983), 1343–1354, and J. Chem. Soc., Perkin Trans 2, 1986, 1337–1344 or can be prepared by the methods described there.

The radical Y is a leaving group, for example the sulfonyl radical or halogen. Preferred sulfonyl radicals are methanesulfonyl, trifluoromethanesulfonyl, benzenesulfonyl and p-toluenesulfonyl and preferred halogens are chlorine and bromine, particularly preferably chlorine.

For the preparation of the novel compounds I by the methods described above, the starting materials are usually used in a stoichiometric ratio. An excess of one or other of the components may be advantageous.

The reactions usually take place at adequate rates at above −20° C. In general, there is no need to exceed 120° C. Since they take place in some cases with evolution of heat, it may be advantageous to provide a means of cooling.

Usually, not less than equivalent amounts of a base are added to II and/or III, but the base may also be used in excess or, if required, as a solvent. Examples of suitable bases are hydroxides of alkali metals and of alkaline earth metals, such as sodium hydroxide, potassium hydroxide and calcium hydroxide, alcoholares of alkali metals and of alkaline earth metals, such as sodium methylate, sodium ethylate, calcium methylate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, and aromatic amines, such as pyridine or pyrrole.

The reaction is advantageously carried out in a solvent or diluent. For example, aliphatic hydrocarbons, such as n-pentane, n-hexane, the hexane isomer mixture and petroleum ether, halohydrocarbons, such as chlorobenzene, methylene chloride, ethylene chloride, chloroform or tetrachloroethylene, aromatic hydrocarbons, such as benzene, toluene, the xylenes and their isomer mixtures or gasoline, alcohols, such as methanol, ethanol, n-propanol or isopropanol, ethers, such as diethyl ether, di-n-butyl ether, methyl tert-butyl ether, tetrahydrofuran or dioxane, ketones, such as acetone, methyl ethyl ketone or methyl isopropyl ketone, nitriles, such as acetonitrile or propionitrile, and aprotic dipolar solvents, such as dimethylformamide, dimethyl sulfoxide or pyridine, are suitable for this purpose. The mixtures of these substances may also be used as solvents and diluents.

Advantageously, the 3(2H)-pyridazinone of the general formula II in a diluent or solvent is initially taken, with subsequent addition of the starting material III. The novel compounds I are isolated by conventional methods. The products obtained may be purified by recrystallization extraction or chromatography.

To prepare the salts, which is possible in the case of suitable hetaryl-substituted isoxazolyl radicals, the corresponding 5-isoxazolyimethyl-3(2H)-pyridazinones I are reacted with conventionally used salt formers, for example hydrochloric acid, hydrobromic acid, hydriodic acid, sulfuric acid, phosphoric acid, formic acid, acetic acid, oxalic acid, benzenesulfonic acid, p-toluene-sulfonic acid, dodecylbenzenesulfonic acid, methyl chloride, methyl bromide, methyl iodide, ethyl chloride, ethyl bromide, ethyl iodide, n-propyl chloride, n-propyl bromide, dimethyl sulfate or diethyl sulfate, at from 0° to 150° C, preferably from 20° to 120° C.

The reaction is advantageously carried out in a solvent or diluent. For example, aliphatic hydrocarbons, such as n-pentane, n-hexane, the hexane isomer mixture or petroleum ether, aromatic hydrocarbons, such as benzene, toluene, the xylenes and their isomer mixtures or gasoline, ethers, such as diethyl ether, di-n-butyl ether, methyl tert-butyl ether, tetrahydrofuran or dioxane, ketones, such as acetone, methyl ethyl ketone or methyl isopropyl ketone, halohydrocarbons, such as chlorobenzene, methylene chloride, ethylene chloride, chloroform or tetrachloroethylene, are suitable for this purpose. Mixtures of these substances can also be used as solvents.

For the preparation of the salts of suitable compounds I by the method described above, the starting materials are usually used in a stoichiometric ratio. However, an excess of one or other of the components may be quite advantageous. The reactions usually take place with sufficient velocity above 0° C. In general, 120° C. need not be exceeded. As heat is evolved in some reactions, it may be advantageous to provide means of cooling.

Conventional methods are employed to isolate the salts of compounds I according to the invention. The products obtained may be purified by recrystallization, extraction or chromatography.

The 3(2H)-pyridazinone derivatives of the formula I are suitable for effectively combating pests such as insects, arachnida, nematodes and snails. They may also be used as pesticides for protecting crop plants, and in the hygiene, stores protection and veterinary sectors.

Examples of injurious insects from the Lepidoptera order are *Agrotis ypsilon, Agrotis segetum, Alabama argillacea,*

*Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Oiaphania nitidalis, Oiatraea grndiosella, Earias insulana, Elasmopalpus lignosellus, Eupoecilia ambiguella, Evetria bouliana, Feltia subterranea, Galleria mellonella, Grapholita funebrana, Grapholita molesta, Helliothis armigera, Hellothis virescens, Heliothis zea, Hellula undalis, Hibernia defoliaria, Hyphantria cunea, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyoneta clerkella, Malacosoma neustria, Hamesira brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Pluteila xylostella, Pseudopiusia includens, Phyacionia frustrana, Scrobipaipula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgilera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex piplens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Franklinleila fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Orthoptera order are *Forficula auricularia, Acheta domestica, Gryllotalpa gryllotalpa, tachycines asynamorus, Locusta migratoria, Stauronotus meroccanus, Schistocerca peregrina, Nomadacris septemfasciata, Melanoplus spretus, Melanoplus femur-rubrum, Blatta orientalis, Blattella germanica, Periplaneta americana* and *Blabera gigantea.*

Examples from the Arachnida order are *Ixodes ficinus, Ornithodorus moubata, Amblyomma americanum, Dermacentor silvarum, Boophilus microplus, Tetranychus telarius, Tetranychus pacificus, Paratetranychus pilosus, Bryobia praetiosa.*

Examples from the Nemathelminthes class are root-knot nematodes, such as *Meloidogyne hapla, Meloidogyne incognita, Meloidogyne javanica,* cyst-forming nematodes, e.g., *Globodera rostochiensis, Heterodera avenae, Hetrodera glycinae, Heterodera schatii, Hetrodera triflolii,* and stem and leaf eelworms, such as *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Paratylenchus neglectus, Paratylenchus penetrans, Paratylenchus curvitatus,* and *Paratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyt alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 6 is intimately mixed with 95 parts by weight of particulate kaolin. A dust is obtained containing 5% by weight of the active ingredient.

II. 30 parts by weight of compound no. 16 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 43 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 126 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 139 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.001 to 0.1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.05 to 2, kg/ha.

The agents according to the invention also have pronounced molluscicidal properties both in slugs and snails, and are excellently suitable for combating snails in agricultural and horticultural crops.

In accordance with the invention, a preparation formulated for example as a broadcasting agent and effective against snails is obtained by employing an effective amount of 3(2H)-pyridazinone derivatives I.

Suitable formulations are described for instance in GB 2,087,723 and EP 190,595. They generally contain a bait, a binder, preservatives, dyes, pheromones, fillers, repellants, water, organic solvents, surfactants and the active ingredient.

As bait, any compound conventionally employed for this purpose may be used. It is preferred to use ground cereals such as wheat meal, coarsely ground wheat, barley and soybeans, bran, rice starch, fish meal, meat meal and molasses. The agent may contain just one bait, or a mixture of several.

Suitable binders are all those conventionally used for such purposes. Examples of preferred binders are methylcellulose, sugar, dextrin, starch, alginates, glycols, polyvinylpyrrolidone, lignin sulfonate, gum arabic, polyvinyl alcohol and polyvinyl acetate. The agent may contain one or several binders.

Examples of preservatives that may be employed are 2-hydoxybiphenyl, sorbic acid, p-hydroxybenzaldehyde, methyl p-hydroxybenzoate, benzaldehyde, benzoic acid, propyl p-hydroxybenzoate and p-nitrophenol.

Examples of dyes suitable as additives are inorganic pigments such as iron oxide, titanium dioxide and iron blue, and organic dyes such as anthraquinone, azo and metal phthalocyanine dyes.

Suitable substances acting as attractants on soil pests are all those conventionally used for this purpose. Examples are aniseed and aniseed oil.

Suitable fillers are all substances conventionally used for this purpose. Preferred fillers are kaolins, diatomaceous earth, talc, chalk and quartz powder.

Suitable substances exhibiting a repellent action on warm-blooded animals such as dogs and hedgehogs are all components conventionally used for this purpose. Nonyl vanillylamide may be mentioned by way of example.

Suitable organic solvents are all those conventionally used for the manufacture of baits. It is preferred to use low-boiling organic solvents such as methanol, ethanol, butanol and methylene chloride.

Suitable surfactants are non-ionic active ingredients such as condensation products of polyalkylene oxides and alkylphenols and fatty acid polyoxyalkylene esters, e.g., octylphenoxypolyoxyethanol; cationic active ingredients such as quaternary ammonium salts, e.g., cetyl trimethylammonium chloride and cetyl pyridinium chloride, and anionic active ingredients such as the sodium salts of long-chain alkyl sulfates, e.g., sodium lauryl sulfate, salts of alkylaryl sulfates, the sodium salt of desoxycholic acid, the sodium salt of taurocholic acid and the sodium salt of tauroglycocholic acid.

Another preferred application form is seed dressing with a formulation conventionally employed for dressings.

The amount of active ingredient in the various application forms may vary within wide limits, e.g., from 0.001 to 90, especially from 0.5 to 50, and preferably from 1 to 10, wt % in granular formulations and from 10 to 90 wt % in seed dressings.

The molluscicidal action of the agents according to the invention extends to both land and amphibious snails, e.g., from the genera Deroceras (Agriolimax), Limax, Helix, Helicogona, Cepaea, Milax, Lymnaea (Galba), Achatina, Theba, Cochlicella, Helicarion and Vaginulus. Examples of snails which cause damage are the slugs *Arion ater*, *A. lusitanicus*, *A. hortensis*, *Agriolimax reticulatus*, *Limax flavus*, *L. maximus*, *Milax gagates*, *Mariella dursumierei*, *Helicarion salius*, *Vaginula hedleyi* and *Pamarion pupillaris*, and the snails Helix aspersa spp., *Cepaea nemoralis*, *Theba pisana*, *Achatina fulica*, *A. zanzibarica*, Bradybaena spp., Cochlodina spp., Helicella spp. and Euomphalia spp.

Formulation Example VI 2 kg of compound no. 43, 8 kg of calcium stearate, 0.2 kg of sodium benzoate, 20 kg of chalk, 0.5 kg of blue dye and 63.3 kg of wheat bran were mixed in a mixer. This mixture was then moistened with sufficient water and kneaded in a kneader. The moist mixture was processed in an extruder to snail bait granules having a diameter of 3 mm, and dried at a maximum temperature of 60° C.

Formulation Example VII

To prepare a seed dressing the following compounds were mixed:

480 g of compound no. 43

20 g of a commercial phenolsulfonic acid-urea-formaldehyde condensate 40 g of an ethylene-propylene block copolymer having a molecular weight of 10,000

2 g of xanthane rubber 0.5 g of Rhodamin FB 80 g of 1,2-propylene glycol 5 g of silicone antifoam and water was added to make up 1 liter.

There may be added to the active ingredients (if desired, immediately before use (tankmix)) oils of various types, herbicides, fungicides, other pesticides and bactericides. These agents may be added to the agents according to the invention in a weight ratio of from 1:10 to 10:1.

Manufacturing examples

I Isoxazolylmethyl-3(2H)-pyridazinone derivatives

Example I.1.

2-tert-Butyl-4-chloro-5-[(3-[2-pyridyl]-isoxazol-5-yl)-methylthio]-3(2 H)-pyradazin-3-one
(compound no. 43)

At room temperature (about 20° C.), 6.32 g (0.0325 mol) of 5-chloromethyl-3-(2-pyridyl)-isoxazole in 20 ml of anhydrous dimethylformamide is dripped into 7.1 g (0.0325 mol) of 2-tert-butyl-4-chloro-5-mercapto-3(2H)-pyridazin-3-one and 4.48 g (0.065 mol) of potassium carbonate in 40 ml of anhydrous dimethylformamide. The mixture is then stirred for 2 hours at 80° C. and overnight at room temperature (about 20° C.). It is then poured into 200 ml of water and extracted with ethyl acetate. The organic phase is dried over magnesium sulfate and the solvent evaporated under reduced pressure. The residue is recrystallized from n-hexane/ethyl acetate (2:1). There is obtained 7.1 g (581% of theory) of 2-tert-butyl-4-chloro-5-[(3-[2-pyridyl]-isoxazol-5-yl)-methylthio]-3(2H)-pyridazin-3-one as a light-colored powder of melting point 99°–102° C.

Example I.2

2-tert-Butyl-4-chloro-5-[(3-[3-pyridyl]-isoxazol-5-yl)-methylthio]-3(2 H)-pyradazin- 3-one
(compound no. 50)

At room temperature (about 20° C.), 8 g (0.042 mol) of 5-chloromethyl-3-(3-pyridyl)-isoxazole in 30 ml of anhydrous dimethylformamide is dripped into 8.96 g (0.042 mol) of 2-tert-butyl-4-chloro-5-mercapto-3(2H)-pyridazin-3-one and 5.66 g (0.082 mol) of potassium carbonate in 50 ml of anhydrous dimethylformamide. The mixture is then stirred overnight at room temperature (20° C.). It is then poured into 200 ml of water and extracted with ethyl acetate. The organic phase is dried over magnesium sulfate and the solvent is evaporated under reduced pressure. The residue is recrystallized from n-hexane/ethyl acetate (4:1). There is obtained 3.8 g (25% of theory) of 2-tert-butyl-4-chloro-5-[(3-[3-pyridyl]-isoxazol-5-yl)methylthio]-3(2H)-pyridazin-3-one as a light-colored powder of melting point 130°–134° C.

Example I.3

Hydrochloride of compound 43 (compound no. 62)

Over a period of 30 minutes, dry hydrogen chloride gas was passed into a solution of 5 g (0.013 mol) of 2-tert-butyl-4-chloro-5-[(3-[2-pyridyl]-isoxazol-5-yl)-methylthio]-3(2H)-pyridazin-3-one in 100 ml of absolute diethyl ether. The white precipitate is removed by suction filtration and dried. There is obtained 4.5 g (85% of theory) of the hydrochloride of compound no. 43 as a hygroscopic powder of melting point 167°–171° C.

The compounds (and salts thereof) given in Table I below may be prepared in accordance with the above directions. The substitution positions on the heterocycles are indicated by a line.

Compounds Ia and salts thereof given in Table 1 below without any physical data may be obtained from the corresponding precursors and are expected to have a similar action.

TABLE 1

Isoxazolylmethyl-3(2H)-pyridazinone derivatives I

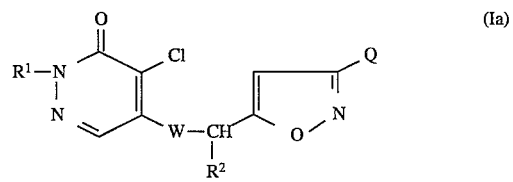

(Ia)

| No. | R$^1$ | R$^2$ | W | Q | Phys. data mp. [°C.] |
|---|---|---|---|---|---|
| 1 | CH$_3$ | H | O | (furyl) | |
| 2 | CH$_3$ | H | S | (thienyl) | |

TABLE 1-continued

Isoxazolylmethyl-3(2H)-pyridazinone derivatives I (Ia)

| No. | R¹ | R² | W | Q | Phys. data mp. [°C.] |
|---|---|---|---|---|---|
| 3 | i-C$_3$H$_7$ | H | O | 2-methylfuran-5-yl | |
| 4 | i-C$_3$H$_7$ | H | S | 2-methylfuran-5-yl | |
| 5 | t-C$_4$H$_9$ | H | O | 2-methylfuran-5-yl | |
| 6 | t-C$_4$H$_9$ | H | S | 2-methylfuran-5-yl | 109–114 |
| 7 | CH$_3$ | H | S | 2-methylfuran-5-yl | |
| 8 | CH$_3$ | H | O | 2-methylthiophen-5-yl | |
| 9 | i-C$_3$H$_7$ | H | O | 2-methylthiophen-5-yl | |
| 10 | i-C$_3$H$_7$ | H | S | 2-methylfuran-5-yl | |
| 11 | t-C$_4$H$_9$ | H | O | 2-methylthiophen-5-yl | |
| 12 | t-C$_4$H$_9$ | H | S | 2-methylthiophen-5-yl | |
| 13 | t-C$_4$H$_9$ | CH$_3$ | S | 2-methylthiophen-5-yl | |
| 14 | CH$_3$ | H | S | 4-bromo-2-methylthiophen-5-yl | |
| 15 | i-C$_3$H$_7$ | H | S | 4-bromo-2-methylthiophen-5-yl | |
| 16 | t-C$_4$H$_9$ | H | S | 4-bromo-2-methylthiophen-5-yl | 110–114 |
| 17 | t-C$_4$H$_9$ | CH$_3$ | S | 4-bromo-2-methylthiophen-5-yl | |
| 18 | t-C$_4$H$_9$ | H | S | 2,3-dimethylthiophen-5-yl | |
| 19 | t-C$_4$H$_9$ | H | S | 2,5-dimethylthiophen-3-yl | |
| 20 | t-C$_4$H$_9$ | H | S | 2-bromo-5-methylthiophen-3-yl | |
| 21 | t-C$_4$H$_9$ | H | S | 2-chloro-5-methylthiophen-3-yl | |
| 22 | t-C$_4$H$_9$ | H | S | 2-nitro-5-methylthiophen-3-yl | |
| 23 | t-C$_4$H$_9$ | H | S | 2,5-dichloro-3-methylthiophen-4-yl | |
| 24 | t-C$_4$H$_9$ | H | S | 3-methylthiophen-2-yl | |
| 25 | t-C$_4$H$_9$ | H | S | 2,5-dimethylfuran-3-yl | |
| 26 | t-C$_4$H$_9$ | H | S | 2-methyl-5-nitrofuran-3-yl | |
| 27 | t-C$_4$H$_9$ | H | S | 1,2-dimethylpyrrol-5-yl | |
| 28 | t-C$_4$H$_9$ | H | S | 1-(4-bromophenyl)-2-methylpyrrol-5-yl | |

TABLE 1-continued

Isoxazolylmethyl-3(2H)-pyridazinone derivatives I (Ia)

| No. | R¹ | R² | W | Q | Phys. data mp. [°C.] |
|---|---|---|---|---|---|
| 29 | t-C₄H₉ | H | S | 1-(2,6-dimethylphenyl)pyrrol-2-yl | |
| 30 | t-C₄H₉ | H | S | 4,5-dimethyl-imidazol-NH | |
| 31 | t-C₄H₉ | H | S | 4-methyl-imidazol-2-yl (NH) | |
| 32 | CH₃ | H | O | 3-methylisoxazol-5-yl | |
| 33 | CH₃ | H | S | 3-methylisoxazol-5-yl | |
| 34 | i-C₃H₇ | H | O | 3-methylisoxazol-5-yl | |
| 35 | i-C₃H₇ | H | S | 3-methylisoxazol-5-yl | |
| 36 | t-C₄H₉ | H | O | 3-methylisoxazol-5-yl | |
| 37 | t-C₄H₉ | H | S | 3-methylisoxazol-5-yl | |
| 38 | CH₃ | H | O | pyridin-2-yl | |
| 39 | CH₃ | H | S | pyridin-2-yl | |
| 40 | i-C₃H₇ | H | O | pyridin-2-yl | |
| 41 | i-C₃H₇ | H | S | pyridin-2-yl | |
| 42 | t-C₄H₉ | H | O | pyridin-2-yl | |
| 43 | t-C₄H₉ | H | S | pyridin-2-yl | 99–102 |
| 44 | t-C₄H₉ | CH₃ | S | pyridin-2-yl | |
| 45 | CH₃ | H | O | pyridin-3-yl | |
| 46 | CH₃ | H | S | pyridin-3-yl | |
| 47 | i-C₃H₇ | H | O | pyridin-3-yl | |
| 48 | i-C₃H₇ | H | S | pyridin-3-yl | |
| 49 | t-C₄H₉ | H | O | pyridin-3-yl | |
| 50 | t-C₄H₉ | H | S | pyridin-3-yl | 130–134 |
| 51 | t-C₄H₉ | CH₃ | S | pyridin-3-yl | |

TABLE 1-continued

Isoxazolylmethyl-3(2H)-pyridazinone derivatives I (Ia)

| No. | R¹ | R² | W | Q | Phys. data mp. [°C.] |
|---|---|---|---|---|---|
| 52 | t-C₄H₉ | CH₃ | O | 3-pyridyl | |
| 53 | CH₃ | H | O | 3-pyridyl | |
| 54 | CH₃ | H | S | 3-pyridyl | |
| 55 | i-C₃H₇ | H | O | 3-pyridyl | |
| 56 | i-C₃H₇ | H | S | 3-pyridyl | |
| 57 | t-C₄H₉ | H | O | 3-pyridyl | |
| 58 | t-C₄H₉ | H | S | 3-pyridyl | 141–144 |
| 59 | t-C₄H₉ | CH₃ | O | 3-pyridyl | |
| 60 | t-C₄H₉ | CH₃ | S | 3-pyridyl | |
| 61 | t-C₄H₉ | H | O | 2-pyridinium·HCl | |
| 62 | t-C₄H₉ | H | S | 2-pyridinium·HCl | 167–171 |
| 63 | t-C₄H₉ | H | O | 3-pyridinium·HCl | |
| 64 | t-C₄H₉ | H | S | 3-pyridinium·HCl | |
| 65 | t-C₄H₉ | H | O | 4-pyridinium·HCl | |
| 66 | t-C₄H₉ | H | S | 4-pyridinium·HCl | |
| 67 | t-C₄H₉ | H | S | tetrahydrofuran-2-yl | |
| 68 | t-C₄H₉ | CH₃ | S | tetrahydrofuran-2-yl | |
| 69 | t-C₄H₉ | H | O | tetrahydrofuran-2-yl | |
| 70 | t-C₄H₉ | CH₃ | O | tetrahydrofuran-2-yl | |
| 71 | t-C₄H₉ | H | O | tetrahydropyran-2-yl | |
| 72 | t-C₄H₉ | CH₃ | O | tetrahydropyran-2-yl | |
| 73 | t-C₄H₉ | H | S | tetrahydropyran-2-yl | |

TABLE 1-continued

Isoxazolylmethyl-3(2H)-pyridazinone derivatives I (Ia)

| No. | R¹ | R² | W | Q | Phys. data mp. [°C.] |
|---|---|---|---|---|---|
| 74 | t-C₄H₉ | CH₃ | S | tetrahydropyran-2-yl | |
| 75 | CH₃ | H | S | tetrahydropyran-2-yl | |
| 76 | i-C₃H₇ | H | S | tetrahydropyran-2-yl | |
| 77 | t-C₄H₉ | H | S | tetrahydropyran-2-yl | 125–127 |
| 78 | t-C₄H₉ | CH₃ | S | tetrahydropyran-2-yl | |
| 79 | t-C₄H₉ | H | S | tetrahydropyran-2-yl | |
| 80 | t-C₄H₉ | CH₃ | S | tetrahydropyran-2-yl | |
| 81 | CH₃ | H | S | tetrahydrothiopyran-2-yl | |
| 82 | i-C₃H₇ | H | S | tetrahydrothiopyran-2-yl | |
| 83 | t-C₄H₉ | H | S | tetrahydropyran-2-yl | |
| 84 | t-C₄H₉ | CH₃ | S | tetrahydrothiopyran-2-yl | |
| 85 | t-C₄H₉ | H | O | tetrahydrothiopyran-2-yl | |
| 86 | t-C₄H₉ | H | S | 1-methylpyrazol-3-yl | |
| 87 | t-C₄H₉ | H | S | 1-methylpyrazol-5-yl | |
| 88 | t-C₄H₉ | H | S | 2-methylpyrazol-3-yl | |
| 89 | t-C₄H₉ | H | S | isoxazol-5-yl | |
| 90 | t-C₄H₉ | H | S | isoxazol-3-yl | |
| 91 | t-C₄H₉ | H | S | isothiazol-5-yl | |
| 92 | t-C₄H₉ | H | S | isothiazol-3-yl | |
| 93 | t-C₄H₉ | H | S | thiazol-2-yl | |
| 94 | t-C₄H₉ | H | S | 1,2,4-oxadiazol-3-yl | |
| 95 | t-C₄H₉ | H | S | oxazol-2-yl | |
| 96 | t-C₄H₉ | H | S | 1,3,4-oxadiazol-2-yl | |
| 97 | t-C₄H₉ | H | S | 1,3,4-thiadiazol-2-yl | |
| 98 | t-C₄H₉ | H | S | pyrazin-2-yl | |

TABLE 1-continued

Isoxazolylmethyl-3(2H)-pyridazinone derivatives I (Ia)

| No. | R¹ | R² | W | Q | Phys. data mp. [°C.] |
|---|---|---|---|---|---|
| 99 | t-C₄H₉ | H | S | (pyrimidine with methyl) | |
| 100 | t-C₄H₉ | H | S | (pyrazine with methyl) | |
| 189 | t-C₄H₉ | H | S | (isoxazole with i-C₃H₇ and methyl) | 93–95 |
| 190 | t-C₄H₉ | H | S | (pyridine with CH₃) | 126–133 |

II. Cycloalkylmethyl-3(2H)-pyridazinone derivatives

Example II.1

2-tert-Butyl-4-chloro-5-[(4-tert-butylcyclohexyl)-methylthio]-3-(2H)-pyridazin-3-one (compound no. 126)

While cooling with ice, 16.61 g (0.055 mol) of [(4-tert-butyl)-cyclohexyl]-methyltrifluoromethane sulfonate in 20 ml of anhydrous dimethylformamide is dripped into 12.05 g (0.055 mol) of 2-tert-butyl-4-chloro-5-mercapto-3(2H)-pyridazin-3-one and 7.6 g (0.11 mol) of potassium carbonate in 50 ml of anhydrous dimethylformamide. The mixture is then stirred overnight at room temperature (about 20° C.). It is then poured into 150 ml of ice water and extracted with ethyl acetate. The organic phases are dried over magnesium sulfate and the solvent is evaporated under reduced pressure. The crude product remaining is purified by flash chromatography on silica gel using n-hexane/ethyl acetate (10:1) as eluant. There is obtained 11.5 g (57% of theory) of 2-tert-butyl-4-chloro-5-[(4-tert-butylcyclohexyl)-methylthio]-3-(2H)-pyridazin-3-one as a viscous oil.

IR absorptions (cm⁻¹): 2963, 2938, 2863, 1654, 1562, 1366, 1213, 1183, 1142, 947

Example II.2

2-tert-Butyl-4-chloro-5-[(2-methoxycyclohexyl)-methylthio]-3-(2H)-pyridazin-3-one (compound no. 139)

While cooling with ice, 8.28 g (0.03 mol) of [(2-methoxy)-cyclohexyl]methyltrifluoromethane sulfonate in 20 ml of anhydrous dimethylformamide is dripped into 6.55 g (0.03 mol) of 2-tert-butyl-4-chloro-5-mercapto-3(2H)-pyridazin-3-one and 4.14 g (0.06 mol) of potassium carbonate in 30 ml of anhydrous dimethylformamide. The mixture is then stirred overnight at room temperature (about 20° C.) and poured into 150 ml of ice water. After extraction with ethyl acetate, the organic phases are dried over magnesium sulfate and the solvent is evaporated off under reduced pressure. The crude product obtained is purified by flash chromatography on silica gel using n-hexane/ethyl acetate (8:1) as eluant. There is obtained 8 g (77% of theory) of 2-tert-butyl-4-chloro-5-[(2-methoxycyclohexyl)-methylthio]-3-(2H)-pyridazin-3-one as a viscous oil.

IR absorptions (cm⁻¹): 2931, 2856, 1654, 1563, 1366, 1183, 1142, 1099, 947

The cycloalkylmethyl-3(2H)-pyridazinone derivatives are in the form of cis-trans diastereomer mixtures, which may, however, be separated into pure diastereomers by conventional methods. The present invention encompasses both the diastereomer mixtures and the pure diastereomers.

Compounds Ia given in Table 2 below without any physical data may be obtained from the corresponding intermediates by the process according to the invention; their action is expected to be similar.

TABLE 2

Cycloalkylmethyl-3(2H)-pyridazinone derivatives Ib

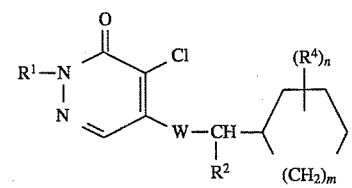

(Ib)

| No. | R¹ | R² | R⁴ | W | m | n | Phys. data IR absorption [cm⁻¹] or mp [°C.] |
|---|---|---|---|---|---|---|---|
| 101 | CH₃ | H | — | S | 2 | 0 | |
| 102 | i-C₃H₇ | H | — | S | 2 | 0 | |
| 103 | i-C₃H₇ | H | — | O | 2 | 0 | |
| 104 | i-C₃H₇ | CH₃ | — | S | 2 | 0 | |
| 105 | t-C₄H₉ | CH₃ | — | S | 2 | 0 | |
| 106 | t-C₄H₉ | H | — | S | 2 | 0 | 66–67 |

TABLE 2-continued

Cycloalkylmethyl-3(2H)-pyridazinone derivatives Ib (Ib)

| No. | $R^1$ | $R^2$ | $R^4$ | W | m | n | Phys. data IR absorption [cm$^{-1}$] or mp [°C.] |
|---|---|---|---|---|---|---|---|
| 107 | CH$_3$ | H | 4-CH$_3$ | S | 2 | 1 | |
| 108 | i-C$_3$H$_7$ | H | 4-CH$_3$ | S | 2 | 1 | |
| 109 | t-C$_4$H$_9$ | H | 4-CH$_3$ | S | 2 | 1 | 1653, 1562, 1142, 947 |
| 110 | CH$_3$ | H | 3-CH$_3$ | S | 2 | 1 | |
| 111 | i-C$_3$H$_7$ | H | 3-CH$_3$ | S | 2 | 1 | |
| 112 | t-C$_4$H$_{99}$ | H | 3-CH$_3$ | S | 2 | 1 | |
| 113 | CH$_3$ | H | 2-CH$_3$ | S | 2 | 1 | |
| 114 | i-C$_3$H$_7$ | H | 2-CH$_3$ | S | 2 | 1 | |
| 115 | t-C$_4$H$_9$ | H | 2-CH$_3$ | S | 2 | 1 | |
| 116 | t-C$_4$H$_9$ | H | 2,4-CH$_3$ | S | 2 | 2 | |
| 117 | t-C$_4$H$_9$ | H | 2,4,6-CH$_3$ | S | 2 | 3 | |
| 118 | t-C$_4$H$_9$ | H | 2-C$_2$H$_5$ | S | 2 | 1 | |
| 119 | t-C$_4$H$_9$ | H | 4-C$_2$H$_5$ | S | 2 | 1 | |
| 120 | CH$_3$ | H | 4-i-C$_3$H$_7$ | S | 2 | 1 | |
| 121 | i-C$_3$H$_7$ | H | 4-i-C$_3$H$_7$ | S | 2 | 1 | |
| 122 | t-C$_4$H$_9$ | H | 4-i-C$_3$H$_7$ | S | 2 | 1 | 1655, 1563, 1452, 1366 |
| 123 | t-C$_4$H$_9$ | H | 4-i-C$_3$H$_7$ | O | 2 | 1 | |
| 124 | CH$_3$ | H | 4-t-C$_4$H$_9$ | S | 2 | 1 | |
| 125 | i-C$_3$H$_7$ | H | 4-t-C$_4$H$_9$ | S | 2 | 1 | |
| 126 | t-C$_4$H$_9$ | H | 4-t-C$_4$H$_9$ | S | 2 | 1 | 1654, 1562, 1366, 1213 |
| 127 | CH$_3$ | H | 3,5-t-C$_4$H$_9$ | S | 2 | 2 | |
| 128 | i-C$_3$H$_7$ | H | 3,5-t-C$_4$H$_9$ | S | 2 | 2 | |
| 129 | t-C$_4$H$_9$ | H | 3,5-t-C$_4$H$_9$ | S | 2 | 2 | |
| 130 | CH$_3$ | H | 4-N(CH$_3$)$_2$ | S | 2 | 1 | |
| 131 | i-C$_3$H$_7$ | H | 4-N(CH$_3$)$_2$ | S | 2 | 1 | |
| 132 | t-C$_4$H$_9$ | H | 4-N(CH$_3$)$_2$ | S | 2 | 1 | |
| 133 | CH$_3$ | H | 4-N(CH$_3$)$_2$ | S | 2 | 1 | |
| 134 | i-C$_3$H$_7$ | H | 4-N(C$_2$H$_5$)$_2$ | S | 2 | 1 | |
| 135 | t-C$_4$H$_9$ | H | 4-N(C$_2$H$_5$)$_2$ | S | 2 | 1 | |
| 136 | CH$_3$ | H | 2-OCH$_3$ | S | 2 | 1 | |
| 137 | i-C$_3$H$_7$ | H | 2-OCH$_3$ | S | 2 | 1 | |
| 138 | t-C$_4$H$_9$ | H | 2-OCH$_3$ | S | 2 | 1 | 1654, 1563, 1183, 1142 |
| 139 | t-C$_4$H$_9$ | H | 2-OC$_2$H$_5$ | S | 2 | 1 | |
| 140 | t-C$_4$H$_9$ | H | 3-OCH$_3$ | S | 2 | 1 | |
| 141 | CH$_3$ | H | 4-OCH$_3$ | S | 2 | 1 | |
| 142 | i-C$_3$H$_7$ | H | 4-OCH$_3$ | S | 2 | 1 | |
| 143 | t-C$_4$H$_9$ | H | 4-OCH$_3$ | S | 2 | 1 | |
| 144 | t-C$_4$H$_9$ | CH$_3$ | 4-OCH$_3$ | S | 2 | 1 | |
| 145 | t-C$_4$H$_9$ | H | 4-OC$_4$H$_9$ | S | 2 | 1 | |
| 146 | t-C$_4$H$_9$ | H | 4-OC$_6$H$_{13}$ | S | 2 | 1 | |
| 147 | CH$_3$ | H | 4-O-t-C$_4$H$_9$ | S | 2 | 1 | |
| 148 | i-C$_3$H$_7$ | H | 4-O-t-C$_4$H$_9$ | S | 2 | 1 | |
| 149 | t-C$_4$H$_9$ | H | 4-O-t-C$_4$H$_9$ | S | 2 | 1 | |
| 150 | t-C$_4$H$_9$ | H | 4-OC$_2$H$_5$ | S | 2 | 1 | |
| 151 | t-C$_4$H$_9$ | H | 2,4-OCH$_3$ | S | 2 | 2 | |
| 152 | t-C$_4$H$_9$ | H | 3,4-OCH$_3$ | S | 2 | 2 | |
| 153 | t-C$_4$H$_9$ | H | 3,5-OCH$_3$ | S | 2 | 2 | |
| 154 | t-C$_4$H$_9$ | H | 3,4,5-OCH$_3$ | S | 2 | 3 | |
| 155 | t-C$_4$H$_9$ | H | 2,4,5-OCH$_3$ | S | 2 | 3 | |
| 156 | t-C$_4$H$_9$ | H | 2,3,4-OCH$_3$ | S | 2 | 3 | |
| 157 | CH$_3$ | H | 4-C(CH$_3$)$_2$OCH$_3$ | S | 2 | 1 | |
| 158 | i-C$_3$H$_7$ | H | 4-C(CH$_3$)$_2$OCH$_3$ | S | 2 | 1 | |
| 159 | t-C$_4$H$_9$ | H | 4-C(CH$_3$)$_2$OCH$_3$ | S | 2 | 1 | 1563, 1452, 1213, 1183 |
| 160 | t-C$_4$H$_9$ | H | 3-F | S | 2 | 1 | |
| 161 | t-C$_4$H$_9$ | H | 3-Cl | S | 2 | 1 | |
| 162 | t-C$_4$H$_9$ | H | 3-Br | S | 2 | 1 | |
| 163 | t-C$_4$H$_9$ | H | 3,5-Cl | S | 2 | 2 | |
| 164 | t-C$_4$H$_9$ | H | 2-CF$_3$ | S | 2 | 1 | 1654, 1454, 1276, 1257 |
| 165 | t-C$_4$H$_9$ | H | 3-CF$_3$ | S | 2 | 1 | 91–94 |
| 166 | CH$_3$ | H | 4-CF$_3$ | S | 2 | 1 | |
| 167 | i-C$_3$H$_7$ | H | 4-CF$_3$ | S | 2 | 1 | |
| 168 | t-C$_4$H$_9$ | H | 4-CF$_3$ | S | 2 | 1 | 1652, 1262, 1143, 1113 |
| 169 | t-C$_4$H$_9$ | H | 4-CF$_2$Cl | S | 2 | 1 | |
| 170 | t-C$_4$H$_9$ | H | 2-OCF$_2$CF$_2$H | S | 2 | 1 | |

TABLE 2-continued

Cycloalkylmethyl-3(2H)-pyridazinone derivatives Ib $$\text{(Ib)}$$

| No. | R¹ | R² | R⁴ | W | m | n | Phys. data IR absorption [cm⁻¹] or mp [°C.] |
|---|---|---|---|---|---|---|---|
| 171 | t-C₄H₉ | H | 3-OCF₂CF₂H | S | 2 | 1 | |
| 172 | CH₃ | H | 4-OCF₂CF₂H | S | 2 | 1 | |
| 173 | i-C₃H₇ | H | 4-OCF₂CF₂H | S | 2 | 1 | |
| 174 | t-C₄H₉ | H | 4-OCF₂CF₂H | S | 2 | 1 | |
| 175 | CH₃ | H | 4-OCHF₂ | S | 2 | 1 | |
| 176 | i-C₃H₇ | H | 4-OCHF₂ | S | 2 | 1 | |
| 177 | t-C₄H₉ | H | 4-OCHF₂ | S | 2 | 1 | |
| 178 | t-C₄H₉ | H | 3-Br, 4-OCH₃ | S | 2 | 2 | |
| 179 | t-C₄H₉ | H | 3-Br, 6-OCH₃ | S | 2 | 2 | |
| 180 | t-C₄H₉ | H | 4-t-C₄H₉ (cis) | S | 2 | 1 | 86 |
| 181 | t-C₄H₉ | H | 4-t-C₄H₉ (trans) | S | 2 | 1 | 111–112 |
| 182 | CH₃ | H | — | O | 1 | 0 | |
| 183 | CH₃ | H | — | S | 1 | 0 | |
| 184 | i-C₃H₇ | H | — | O | 1 | 0 | |
| 185 | i-C₃H₇ | H | — | S | 1 | 0 | |
| 186 | t-C₄H₉ | H | — | O | 1 | 0 | |
| 187 | t-C₄H₉ | H | — | S | 1 | 0 | |
| 188 | i-C₃H₇ | H | 3-CF₃ | S | 2 | 1 | 1649, 1629, 1285, 1268 |

Use examples

In the following examples, the compounds were investigated as to their action on *Tetranychus telarius, Aphis fabae,* and *Dysdercus intermedius*. The purity of the active ingredients was >95%.

The formulation employed was an emulsion concentrate containing 10wt % of active ingredient. This concentrate was obtained by adding the active ingredient to a mixture of 70wt % of cyclohexanone, 20wt % of NeKanil LN® (≙ Lutensol AP6, a spreader-sticker based on ethoxylated alkylphenols and having an emulsifying and dispersant action) and 10wt % of Emulphor EL® (= Emulan El®, an emulsifier based on ethoxylated fatty alcohols). The concentrations given in the examples were obtained by diluting the formulated active ingredient with water.

Example A

Contact action on *Aphis fabae*; spray experiment

Young bean plants (*Vicia faba*) heavily infested by a colony of *Aphis fabae* are sprayed from all sides with about 50 ml of the aqueous active ingredient formulations. The percentage kill is assessed after 24 hours.

In this experiment, the compounds of Examples 16 and 106 have a good action.

Example B

*Tetranychus telarius* a) Potted bush beans exhibiting the second pair of true leaves are sprayed to runoff in a spray cabinet with aqueous formulations of the active ingredients. The plants are placed on a rotating table and are sprayed from all sides with a total of 50 ml of spray liquor. The plants are under heavy mite attack and bear numerous eggs.

The action is assessed after 5 days by means of a binocular microscope.

In this experiment, the compounds of Examples 43, 122, 126, 159 and 164 exhibit a good action.

b) Potted bush beans exhibiting the second pair of true leaves are sprayed to runoff in a spray cabinet with aqueous formulations of the active ingredients. The plants are placed on a rotating table and are sprayed from all sides with a total of 50 ml of spray liquor. After 24 hours, leaf pieces under heavy mite attack are placed on the plants. The action is assessed after 12 days.

In this experiment, the compounds of Examples 43, 122, 126 and 159 have a good action.

Example C

Ovicidal action on *Dysdercus intermedius*

Pieces of adhesive tape (about 0.8 cm) are stuck to the top edge of plastic plant markers. 24 hours before commencement of the experiment, eggs of the cotton stainer contained in a vessel are attached to the adhesive strips by dipping the markers into the vessel.

The eggs are then dipped for 5 seconds into aqueous formulations of the active ingredients and excess liquid is allowed to drip off onto filter paper.

The markers are placed (adhesive tape up) in plastic pallets which are covered with a glass plate. Care is taken during the experiment to provide sufficient moisture to prevent drying out.

Assessment takes place after about 8 days (after the larvae in the control batch have hatched).

In this experiment, the compounds of Examples 43 and 159 have a good action.

We claim:

1. 2-(3H)-Pyridazinone compounds of the formula I

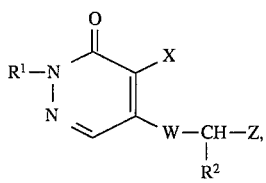 (I)

where $R^1$ is $C_1-C_8$-alkyl, $R^2$ is hydrogen or $C_1-C_4$-alkyl, X is halogen, W is oxygen or sulfur and Z is an isoxazolyl radical of the formula

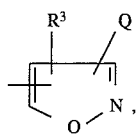

where $R^1$ is hydrogen, halogen, $C_1-C_8$-alkyl or $C_2-C_8$-alkenyl and Q is a 5-membered or 6-membered heterocyclic structure bonded to a ring carbon of the said isoxazolyl radical selected from the group consisting of furan-2-yl, thiophen-2-yl, isoxazol-5-yl, pyridin-2-yl, pyridin-3-yl, pyridin-4-yl and tetrahydropyran-4-yl, which structure is unsubstituted or monosubstituted to trisubstituted on a carbon or nitrogen of said structure by halogen, $C_1-C_8$-alkyl, $C_2-C_6$-alkenyl, $C_1-C_4$-haloalkyl, $C_1-C_8$-alkoxy, $C_2-C_8$-alkoxyalkyl, $C_3-C_8$-cycloalkyl, or monosubstituted by cyano or nitro, and plant-tolerated salts thereof.

2. A pesticidal agent containing a 3(2H)-pyridazinone compound of the formula I as set forth in claim 1 in addition to solid or liquid carriers.

3. A pesticidal agent as set forth in claim 2, containing from 0.1 to 95 wt % of a 3(2H)-pyridazinone compound of the formula I.

4. Snail baits containing a molluscicidally effective amount of a 3(2H)-pyridazinone compound of the formula I of claim 1.

5. Seed dressings containing a pesticidally effective amount of a 3(2H)-pyridazinone compound of the formula I of claim 1.

6. A process for combatting insects, arachnida, nematodes and snails, wherein these pests and/or spaces are treated with a pesticidally effective amount of a 3(2H)-pyridazinone compound of the formula I as set forth in claim 1.

* * * * *

UNITED STATES PATENT AND TRADEMARK OFFICE
CERTIFICATE OF CORRECTION

PATENT NO.: 5,541,185

DATED: July 30, 1996

INVENTOR(S): LEYENDECKER et al.

It is certified that error appears in the above-identified patent and that said Letters Patent is hereby corrected as shown below:

Column 27, claim 1, line 22, "$R^1$" should be --$R^3$--.

Signed and Sealed this

Fifth Day of November, 1996

Attest:

BRUCE LEHMAN

Attesting Officer

Commissioner of Patents and Trademarks